United States Patent [19]

Ingle

[11] 4,237,120

[45] Dec. 2, 1980

[54] ANTIBACTERIAL AGENT BM123-GAMMA, PHARMACEUTICALLY ACCEPTABLE SALTS, COMPLEXES AND ALKYLATED DERIVATIVES AS ANIMAL FOOD ADDITIVES

[75] Inventor: Donald L. Ingle, Trenton, N.J.

[73] Assignee: American Cyanamid Company, Stamford, Conn.

[21] Appl. No.: 70,458

[22] Filed: Aug. 28, 1979

Related U.S. Application Data

[63] Continuation-in-part of Ser. No. 874,432, Feb. 2, 1978, abandoned.

[51] Int. Cl.$^3$ ............................................. A61K 31/71
[52] U.S. Cl. ..................................................... 424/181
[58] Field of Search ......................................... 424/181

[56] References Cited

U.S. PATENT DOCUMENTS

| | | | |
|---|---|---|---|
| 3,577,529 | 5/1971 | Pensack | 424/181 |
| 3,579,635 | 5/1971 | Raun et al. | 424/181 |
| 4,007,167 | 2/1977 | Martin et al. | 424/181 X |
| 4,018,972 | 4/1977 | Hlavka | 424/181 |
| 4,053,592 | 10/1977 | Smith | 424/181 |

*Primary Examiner*—Frederick E. Waddell
*Attorney, Agent, or Firm*—H. G. Jackson

[57] ABSTRACT

This disclosure relates to novel methods of use to improve feed efficiency and to enhance the growth rate of meat animals comprising administering to the animals an effective amount of antibacterial cis-BM123γ and/or antibacterial trans-BM123γ or the pharmaceutically acceptable salts, complexes, or alkylated derivatives thereof in the animals feed.

29 Claims, No Drawings

ANTIBACTERIAL AGENT BM123-GAMMA, PHARMACEUTICALLY ACCEPTABLE SALTS, COMPLEXES AND ALKYLATED DERIVATIVES AS ANIMAL FOOD ADDITIVES

This application is a continuation-in-part of copending Ser. No. 874,432 filed Feb. 2, 1978 now abandoned.

Antibacterial trans-BM123γ is formed by fermentative biosynthesis during the cultivation under controlled conditions of new strains of an undetermined species of Nocardia NRRL 5646, NRRL 8050, NRRL 11,230 and mutants thereof. The preparation and properties of antibacterials trans-BM123γ, trans-BM123γ$_1$, and trans-BM123γ$_2$ are set forth in U.S. Pat. No. 4,007,167 which is hereby incorporated by reference. Antibacterial cis-BM123γ is formed by the photochemical transformation of the corresponding trans-isomer. The preparation and properties of antibacterials cis-BM123γ, cis-BM123γ$_1$, and cis-BM123γ$_2$ are set forth in U.S. Pat. No. 4,018,972 which is also hereby incorporated by reference. Hereinafter, trans-BM123γ refers to a mixture in any proportions of trans-BM123γ$_1$ and trans-BM123γ$_2$ whereas cis-BM123γ refers to a mixture in any proportions of cis-BM123γ$_1$ and cis-BM123γ$_2$. The term cis-BM123γ and/or trans-BM123γ refers to the use of cis-BM123γ alone, or of trans-BM-123γ alone, or of a mixture in any proportions of cis-BM123γ and trans-BM123γ.

Until recently, a number of animal growth-promoting agents such as the tetracycline-type antibiotics, penicillin and zinc bacitracin, and hormonal agents such as diethylstilbestrol, have been used successfully to improve feed efficiency and increase the growth rate of meat animals. However, with the increasing demand for greater food production, and increasing animal production costs, it is now imperative that new methods and compositions be provided which will enhance the growth rate of meat animals and improve feed conversion (i.e. the ratio of unit weight of feed consumed per unit weight of gain) in the raising of the meat animals.

Surprisingly, we have discovered that in meat animals feed efficiency in the raising of poultry, such as chickens and turkeys, and in other meat animals, such as sheep, cattle, swine and goats, can be improved by orally administering to the host animal an effective amount of antibiotic cis-BM123γ and/or antibiotic trans-BM123γ or the pharmaceutically acceptable salts, complexes or alkylated derivatives thereof. We have also found that the administration of said agents measurably enhances the growth rate of animals.

In accordance with this invention, the growth rate of meat animals, such as poultry, sheep, cattle, swine and goats is measurably improved when antibiotic cis-BM123γ and/or antibiotic trans-BM123γ, or the pharmaceutically acceptable salts, complexes or alkylated derivatives thereof is administered to the above-said host animal in or with the feed in an amount equivalent to between 0.0001% to 1.00% (1–10000 ppm). The preferred amount for poultry is 0.001% to 0.01% (1–100 ppm); for cattle and sheep the preferred amount is 0.0001% to 0.1% (1–1000 ppm); and for swine the preferred amount is 0.0001% to 0.01% (1–100 ppm) by weight of feed.

In practice, the active material will generally be formulated as a premix and/or animal feed supplement which is admixed with a nutritionally balanced feed or added to the feed as a top dressing, or the like. Premixes may be prepared by blending about 70% to 99% by weight of rice flour, ground rice hulls, ground corn, or the like with about 1% to 30% by weight of the active material. Pharmaceutically acceptable salts of cis-BM123γ and/or trans-BM123γ which may be employed in practicing the present invention are set forth in the aforementioned U.S. Pat. Nos. 4,007,167 and 4,018,972.

The above referred-to complexes of cis-BM123γ and/or trans-BM123γ may be prepared by reacting the antibiotic with an alkali metal alkyl sulfate of formula $CH_3(CH_2)_n$—$OSO_3M$ wherein M is sodium or potassium and n is an integer from 9 to 17. Among the compounds represented by the above formula, sodium decyl sulfate, sodium lauryl sulfate and sodium cetyl sulfate are preferred. Antibiotic cis-BM123γ and/or trans-BM123γ-dioctyl sodium or calcium sulfosuccinate complexes may be prepared by similar methods.

The antibiotic also forms complexes with "syntan" compounds. Syntan compounds are synthetic tanning agents of sulfated phenol formaldehyde condensate type, which may be represented by the following general formula:

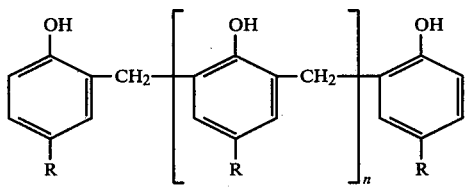

wherein R is hydrogen or methylene sulfonic acid (—$CH_2SO_3H$); n is 0,/1, 2, 3 or 4 with the proviso that about half of the R groups present are methylene sulfonic acid groups. This synthetic tanning agent is not a pure chemical compound but of necessity is obtained as a mixture having an estimated molecular weight of 420–530. It is readily prepared by first condensing phenol and formaldehyde in aqueous media followed by reaction of the intermediate condensate with formaldehyde, various sulfites and buffer acids thus forming ω-sulfonic acid groups (—$CH_2SO_3H$) in the molecules. The product is an amorphous water-soluble material that may be obtained either in concentrated water solution or in powder form, and ranges from colorless to dark brown. In order to avoid cumbersome language, this synthetic tanning agent is referred to by its generic name in the art as "syntan" and this term is used in the specification and appended claims. A sulfated phenol formaldehyde syntan of the above general formula is sold by A. J. and J. O. Pilar Inc. of Newark, N.J. under the trade name Tru-Tan ® RT New.

The above complexes have been referred to as reversible antibiotic-alkyl sulfate, antibiotic-dioctyl sulfosuccinate and antibiotic-syntan complexes. Their exact chemical nature has not been determined, but covalent bonding is not involved and the products are not physical mixtures nor are they necessarily combined in any limiting stoichiometry. The chemical bonds are reversible since the antibiotic may be recovered from the complexes by various means.

It seem possible that the above complexes of antibiotic cis-BM123γ and/or antibiotic trans-BM123γ of the present invention are sufficiently reversible so that under conditions of use in animal feed compositions the antibiotic is set free upon ingestion.

The alkylated derivatives of trans-BM123γ which are effective as growth promoting agents for the above-mentioned farm animals are described in U.S. Pat. No. 4,048,431 and illustrated as formula's I, II, III and IV therein. Particularly effective as animal growth promoting agents are those represented by formula I, having the structure:

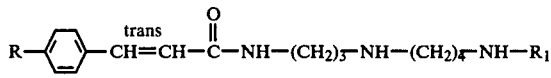

wherein $R_1$ is alkyl $C_1$-$C_{10}$, halosubstituted alkyl $C_2$-$C_6$, or hydroxysubstituted alkyl $C_2$-$C_6$ and wherein R is a moiety selected from the group consisting of those of the formula:

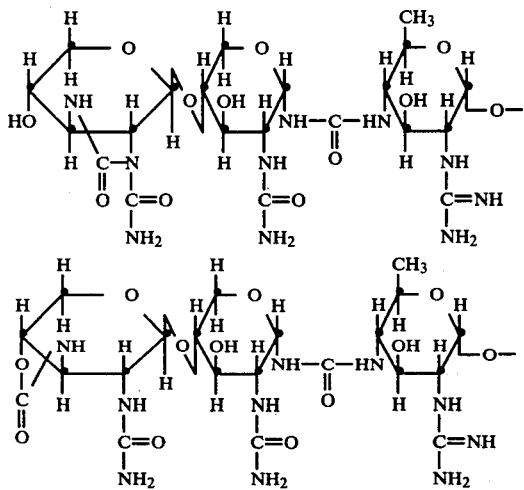

The alkylated derivatives of cis-BM123γ may be prepared from cis-BM123γ itself in a manner exactly comparable to that employed for the trans-isomer. Alternatively, they may be prepared by photochemical transformation of the alkylated derivatives of trans-BM123γ.

Should it be desired, the antibiotic cis-BM123γ and/or antibiotic trans-BM123γ, the salts, complexes and alkylated derivatives thereof may also be administered to said meat animals in their drinking water. Alternatively, pills, tablets, boluses and the like, containing the above active compounds and suitable for oral administration, may be prepared by known pharmaceutically acceptable methods. However, oral administration of said growth-promoting antibiotics to the host animals in, or with their feed is preferred.

The following non-limiting examples serve to further illustrate the novel methods of the present invention.

EXAMPLE 1

Evaluation of trans-BM123γ-hydrochloride as a feed additive for the enhancement of the growth rate of poultry.

Test Drug

Trans-BM123γ-hydrochloride mixture administered to the test animals in their feed at levels of 10, 20 and 40 ppm.

Test Animals

One day old Hubbard X Hubbard Crossbred Chicks, randomly allotted to pens of ten chicks (5 males and 5 females) each.

Procedure

Four experiments are started at one week intervals. In each experiment, four pens of chicks are used for unmedicated controls, and four pens of chicks are used at each level of drug. Thus in this set of experiments a total of 16 pens (160 chicks) are used as controls, and a total of 16 pens (160 chicks) are used at each level of drug. The duration of each experiment is 13 days.

The controls are offered an unmedicated diet of Broiler ration No. 453 (composition appended hereto) and water ad libitum. Medicated chicks are offered the same diet containing the test drug at the levels indicated above, and water ad libitum. The weight of the chicks is determined at the beginning and on completion of the experiments. Weight gains and the amount of feed consumed are also determined. The thus obtained data are averaged and summarized in Table I below, wherein the percent improvement in weight gains and feed/gain ratios is also given.

| Broiler Ration No. 453 | |
| --- | --- |
| Component | Percent by weight |
| Ground yellow corn | 53.45 |
| Soybean oil meal (49%) | 28.00 |
| Menhaden fish meal (60%) | 5.00 |
| Corn Gluten meal (60%) | 5.00 |
| Dehydrated Alfalfa meal (17%) | 2.00 |
| Stabilized fat | 4.00 |
| Dicalcium phosphate | 1.20 |
| Ground limestone | 0.50 |
| Sodium chloride | 0.30 |
| Trace Minerals mixture* | 0.05 |
| Vitamin premix** | 0.50 |
| | 100.00 |

| *Trace Mineral Mixture | | 1 lb/ton furnishes |
| --- | --- | --- |
| Manganese | 12.50% | 62.5 ppm |
| Iron | 6.00 | 30.0 |
| Zinc | 5.00 | 25.0 |
| Copper | 0.65 | 3.25 |
| Iodine | 0.35 | 1.75 |
| Cobalt | 0.25 | 1.25 |
| Calcium min. | 15.30 | |
| max. | 18.35 | |

| **Vitamin Premix for 1-ton | Weight in gram |
| --- | --- |
| DL Methionine | 453.6 |
| BHT (Butylated Hydroxy toluene) | 113.6 |
| Vitamin A (30,000 mcg/g) | 100.0 |
| Vitamin D3 (200,000 mcg/g) | 5.0 |
| Vitamin E (20,000 mcg/lb) | 45.4 |
| Riboflavin | 4.0 |
| Niacinamide | 25.0 |
| Calcium Pantothenate | 8.0 |
| Vitamin K (menadione) | 1.0 |
| Parvo (10%), folic acid | 13.0 |
| Choline Chloride (50%) | 908.0 |
| Proferm (20 mg/lb), B12 | 227.0 |
| Corn oil | 50.0 |
| Fine ground corn | 2,582.4 |
| | 4,536.0 |

TABLE I

Evaluation of the Efficacy of Trans-BM123γ-hydrochloride as a Feed Additive for the Enhancement of the Growth Rate and for increasing Feed Efficiency of Broilers fed for 13 days.

| Treatment | Drug Level in Feed (ppm) | Average weight per Chick in Gram Start | Average weight per Chick in Gram End | Average weight gain per Chick in Gram | Feed Consumed per Chick in Gram (Average) | Feed/Gain Ratio | Percent Improvement in Gain | Percent Improvement in Feed/Gain Ratio |
| --- | --- | --- | --- | --- | --- | --- | --- | --- |
| Control | 0 | 38.8 | 211.7 | 172.9 | 273.7 | 1.583 | | |
| Trans- | 10 | 38.8 | 231.5 | 192.7 | 277.5 | 1.440 | 11.5 | 9.9 |
| BM123γ- | 20 | 38.8 | 226.1 | 187.3 | 281.6 | 1.503 | 8.3 | 5.3 |
| hydrochloride mixture | 40 | 38.7 | 227.2 | 188.4 | 275.4 | 1.462 | 9.0 | 8.3 |

EXAMPLE 2

Evaluation of trans-BM123γ-hydrochloride as a feed additive for the enhancement of the growth rate of poultry.

Test Drug

Trans-BM123γ-hydrochloride mixture administered to the test animals in their feed 1t levels of 1, 2, 5, 10 and 20 ppm.

Test Animals

One day old Hubbard X Hubbard Crossbred Chicks, randomly allotted to pens of ten chicks (5 males and 5 females) each.

Procedure

Eight pens of chicks are used for unmedicated controls, and four pens of chicks are used at each level of drug. The duration of the experiment is 28 days.

The controls are offered an unmedicated diet of Broiler ration No. 453 (composition given in Example I) and water ad libitum. Medicated chicks are offered the same diet containing the test drug at the levels indicated above, and water ad libitum. The weight of the chicks is determined at the beginning and on completion of the experiments. Weight gains and the amount of feed consumed are also determined. The thus obtained data are averaged and summarized in Table II below, wherein the percent improvement in weight gains and feed/gain ratios is also given.

TABLE II

Evaluation of the Efficacy of Trans-BM123γ-hydrochloride as a Feed Additive for the Enhancement of the Growth Rate and for Improving Feed Efficiency of Broilers fed for 28 days.

| Treatment | Drug Level in Feed (ppm) | Average weight per Chick in Gram Start | Average weight per Chick in Gram End | Average weight gain per Chick in Gram | Feed Consumed per Chick in gram (Average) | Feed/Gain Ratio | Percent Improvement in Gain | Percent Improvement in Feed/Gain Ratio |
| --- | --- | --- | --- | --- | --- | --- | --- | --- |
| Control | 0 | 42.8 | 767.5 | 722.5 | 1119.9 | 1.550 | | |
| Trans- | 1 | 42.8 | 757.3 | 714.5 | 1095.3 | 1.533 | −1.1 | 1.1 |
| BM123γ | 2 | 42.8 | 787.2 | 744.4 | 1111.4 | 1.493 | 3.0 | 3.7 |
| hydrochloride | 5 | 42.8 | 785.8 | 743.0 | 1116.0 | 1.502 | 2.8 | 3.1 |
| | 10 | 42.7 | 809.0 | 766.2 | 1155.4 | 1.508 | 6.1 | 2.7 |
| | 20 | 42.8 | 795.6 | 752.7 | 1128.3 | 1.499 | 4.2 | 3.3 |

EXAMPLE 3

Evaluation of various salts of trans-BM123γ as feed additives for the enhancement of the growth rate of poultry

Test Drugs

1. Trans-BM123γ-hydrochloride.
2. Trans-BM123γ-sodium lauryl sulfate precipitate.
3. Trans-BM123γ-Tru-Tan ® precipitate.

The above drugs are administered to the test animals in their feed at the levels indicated in Table III below.

Test Animals

One day old Hubbard X Hubbard crossbred chicks, randomly allotted to pens of ten chicks (5 males and 5 females) each.

Procedure

The procedure of Example I is used, except that two pens of chicks are used at each level of drug. Thus in this set of experiments a total of 16 pens (160 chicks) are used as controls and a total of 8 pens (80 chicks) are used at each level of drug. The duration of each experiment is 13 days.

The data obtained are averaged and summarized in Table III below, wherein the percent improvement in weight gains, and in feed/gain ratios is also given.

TABLE III

Evaluation of the Efficacy of Various salts of Antibiotic trans-BM123γ for the Enhancement of the Growth Rate of Poultry and for Improving Feed Efficiency.

| Treatment | Drug Level in Feed (ppm) | Average weight per Chick in Gram Start | Average weight per Chick in Gram End | Average weight gain per Chick in Gram | Feed Consumed per Chick in Gram (Average) | Feed/Gain Ratio | Percent Improvement in Gain | Percent Improvement in Feed/Gain Ratio |
| --- | --- | --- | --- | --- | --- | --- | --- | --- |
| Control | 0 | 44.0 | 239.3 | 195.4 | 292.1 | 1.495 | | |
| Antibiotic trans-BM123γ | 5 | 44.1 | 248.3 | 204.3 | 297.9 | 1.458 | 4.6 | 2.5 |

TABLE III-continued

Evaluation of the Efficacy of Various salts of Antibiotic trans-BM123γ for the Enhancement of the Growth Rate of Poultry and for Improving Feed Efficiency.

| Treatment | Drug Level in Feed (ppm) | Average weight per Chick in Gram Start | Average weight per Chick in Gram End | Average weight gain per Chick in Gram | Feed Consumed per Chick in Gram (Average) | Feed/Gain Ratio | Percent Improvement in Gain | Percent Improvement in Feed/Gain Ratio |
|---|---|---|---|---|---|---|---|---|
| hydrochloride | 10 | 44.0 | 246.4 | 202.5 | 293.6 | 1.450 | 3.6 | 3.0 |
| mixture | 20 | 44.1 | 258.5 | 214.4 | 301.7 | 1.407 | 9.7 | 5.9 |
| Antibiotic | 1 | 44.0 | 239.9 | 195.9 | 287.2 | 1.466 | 0.3 | 1.9 |
|  | 2 | 44.0 | 237.6 | 193.6 | 292.5 | 1.511 | −0.9 | −1.1 |
| trans-BM123γ | 5 | 44.0 | 246.5 | 202.5 | 297.5 | 1.469 | 3.6 | 1.7 |
|  | 10 | 44.0 | 246.8 | 202.8 | 292.0 | 1.440 | 3.8 | 3.7 |
| Lauryl sulfate | 20 | 44.0 | 257.7 | 213.8 | 303.4 | 1.419 | 9.4 | 5.1 |
|  | 30 | 44.0 | 248.2 | 204.3 | 293.4 | 1.436 | 4.6 | 3.9 |
| Antibiotic | 1 | 44.1 | 245.2 | 201.2 | 294.0 | 1.461 | 3.0 | 2.3 |
|  | 2 | 44.0 | 244.4 | 200.4 | 296.2 | 1.478 | 2.6 | 1.1 |
| trans-BM123γ | 5 | 44.0 | 249.4 | 205.4 | 292.9 | 1.426 | 5.1 | 4.6 |
|  | 10 | 44.0 | 251.8 | 207.8 | 299.6 | 1.442 | 6.3 | 3.5 |
| Tru-Tan ® | 20 | 44.0 | 251.8 | 207.8 | 302.1 | 1.454 | 6.3 | 2.7 |
|  | 30 | 44.0 | 248.1 | 204.1 | 294.9 | 1.445 | 4.5 | 3.3 |

EXAMPLE 4

Evaluation of antibiotic trans-BM123γ-hydrochloride as a feed additive for the enhancement of the growth rate of poultry

Test Drugs

1. Antibiotic trans-BM123γ-hydrochloride, purified.
2. Antibiotic trans-BM123γ-hydrochloride, obtained by spray-drying the as is fermentation mash.

The above drugs are administered to the test animals in their feed at the levels indicated in Table IV below.

Test Animals

One day old Hubbard X Hubbard Crossbred chicks, randomly allotted to pens of ten chicks (5 males and 5 females) each.

Procedure

The procedure of Example I is used, except that two pens of chicks are used at each level of drug. Thus in this set of experiments a total of 16 pens (160 chicks) are used as controls and a total of 8 pens (80 chicks) are used at each level of drug. The duration of each experiment is 13 days.

The data obtained are averaged and summarized in Table IV below, wherein the present improvement in weight gains, and in feed/gain ratios is also given.

TABLE IV

Evaluation of the Efficacy of Antibiotic trans-BM123γ-hydrochloride samples, obtained by different methods, for the Enhancement of the Growth Rate of Poultry and for Improving Feed Efficiency.

| Treatment | Drug Level in Feed (ppm) | Average weight per Chick in Gram Start | Average weight per Chick in Gram End | Average weight gain per Chick in Gram | Feed Consumed per Chick in gram (Average) | Feed/Gain Ratio | Percent Improvement in Gain | Percent Improvement in Feed/Gain Ratio |
|---|---|---|---|---|---|---|---|---|
| Control | 0 | 43.7 | 234.1 | 190.4 | 294.4 | 1.546 |  |  |
| Antibiotic | 2 | 43.7 | 229.9 | 186.2 | 288.2 | 1.548 | −2.2 | −0.1 |
| trans-BM123γ | 5 | 43.7 | 238.4 | 194.7 | 293.0 | 1.505 | 2.3 | 2.7 |
| hydrochloride | 10 | 43.7 | 242.2 | 198.5 | 295.2 | 1.487 | 4.3 | 3.8 |
|  | 20 | 43.8 | 245.3 | 201.6 | 297.2 | 1.474 | 5.9 | 4.7 |
| Antibiotic* | 1 | 43.8 | 233.6 | 189.9 | 291.5 | 1.535 | −0.3 | 0.7 |
| trans-BM123γ | 2 | 43.7 | 236.1 | 192.4 | 291.5 | 1.515 | 1.1 | 2.0 |
| hydrochloride | 5 | 43.8 | 245.0 | 201.3 | 296.9 | 1.475 | 5.7 | 4.6 |
|  | 10 | 43.7 | 249.7 | 206.0 | 295.0 | 1.432 | 8.2 | 7.4 |
|  | 20 | 43.7 | 251.9 | 208.2 | 301.9 | 1.450 | 9.3 | 6.2 |

*Spray-dried fermentation mash.

EXAMPLE 5

Evaluation of antibiotic trans-BM123γ-hydrochloride as feed additives for the enhancement of the growth rate of poultry

Test Drug

Sample #1. Antibiotic trans-BM123γ-hydrochloride, low γ₂ content.
Sample #2. Antibiotic trans-BM123γ-hydrochloride, high γ₂ content.

The drug samples are administered to the test animals in their feed at the levels indicated in Table V below.

Test Animals

One day old Hubbard X Hubbard crossbred chicks, randomly allotted to pens of ten chicks (5 males and 5 females) each.

Procedure

The procedure of Example I is used. The duration of each experiment is 14 days.

The data obtained are averaged and summarized in Table V below, wherein the percent improvement is weight gains, and in feed/gain ratios is also given.

TABLE V

Evaluation of the Efficacy of Antibiotic trans-BM123γ-hydrochloride samples of various isomeric composition, for the Enhancement of the growth rate of poultry, and for Improving Feed Efficiency.

| Treatment | Drug Level in Feed (ppm) | Average weight per Chick in Gram Start | Average weight per Chick in Gram End | Average weight gain per Chick in Gram | Feed Consumed per Chick in gram (Average) | Feed/Gain Ratio | Percent Improvement in Gain | Percent Improvement in Feed/Gain Ratio |
| --- | --- | --- | --- | --- | --- | --- | --- | --- |
| Control | 0 | 42.4 | 271.5 | 229.1 | 342.0 | 1.493 | | |
| Antibiotic trans-BM123γ hydrochloride Sample #1 | 10 | 42.4 | 279.9 | 237.4 | 344.5 | 1.451 | 3.6 | 2.8 |
| | 20 | 42.4 | 282.0 | 239.7 | 347.6 | 1.450 | 4.6 | 2.9 |
| Antibiotic trans-BM123γ hydrochloride Sample #2 | 5 | 42.3 | 275.9 | 233.6 | 341.5 | 1.462 | 2.0 | 2.1 |
| | 10 | 42.3 | 274.1 | 231.8 | 332.2 | 1.433 | 1.2 | 4.0 |
| | 20 | 42.4 | 285.8 | 243.5 | 344.8 | 1.416 | 6.3 | 5.2 |

EXAMPLE 6

Evaluation of antibiotic trans-BM123γ-salts as feed additives for the enhancement of the growth rate of poultry Test Drug Sample #1. Antibiotic trans-BM123γ-hydrochloride.

Sample #2. Antibiotic trans-BM123γ-precipitated from crude fermentation mash with sodium lauryl sulfate.

Sample #3. Antibiotic trans-BM123γ-precipitated from fermentation mash filtrate with sodium lauryl sulfate.

The above drugs are administered to the test animals in their feed at the levels indicated in Table VI below.

Test Animals

One day old Hubbard X Hubbard crossbred chicks, randomly allotted to pens of ten chicks (5 males and 5 females) each.

Procedure

The procedure of Example 3 is used. The duration of each experiment is 14 days.

The data obtained are averaged and summarized in Table VI below, wherein the percent improvement in weight gains, and in feed/gain ratios is also given.

EXAMPLE 7

Evaluation of Antibiotic trans-BM123γ salts as feed additives for the enhancement of the growth rate of poultry Test Drug

1. Antibiotic trans-BM123γ-hydrochloride.

2. Antibiotic trans-BM123γ-precipitated from crude fermentation mash with sodium lauryl sulfate.

3. Antibiotic trans-BM123γ-precipitated from fermentation mash filtrate with sodium lauryl sulfate.

4. Antibiotic trans-BM123γ-precipitated from fermentation mash filtrate with sodium dioctyl sulfosuccinate.

The above drugs are administered to the test animals in their feed at the levels indicated in Table VII below.

Test Animals

One day old Hubbard X Hubbard crossbred chicks, randomly alloted to pens of ten chicks (5 males and 5 females) each.

Procedure

The procedure of Example 6 is used. The duration of the experiment is 14 days.

The data obtained are averaged and summarized in Table VII below, wherein the percent improvement in weight gains, and in feed/gain ratios is given.

TABLE VI

Evaluation of the Efficacy of various samples of Antibiotic trans-BM123γ for the Enhancement of the Growth rate of poultry, and for Increasing Feed Efficiency.

| Treatment | Drug Level in Feed (ppm) | Average weight per Chick in Gram Start | Average weight per Chick in Gram End | Average weight gain per Chick in Gram | Feed Consumed per Chick in Gram (Average) | Feed/Gain Ratio | Percent Improvement in Gain | Percent Improvement in Feed/Gain Ratio |
| --- | --- | --- | --- | --- | --- | --- | --- | --- |
| Control | 0 | 41.1 | 291.2 | 250.1 | 344.9 | 1.379 | | |
| Antibiotic trans-BM123γ Sample #1 | 10 | 41.1 | 306.6 | 265.6 | 355.6 | 1.339 | 6.2 | 2.9 |
| | 20 | 41.1 | 294.1 | 253.0 | 346.9 | 1.371 | 1.2 | 0.6 |
| Antibiotic trans-BM123γ Sample #2 | 5 | 41.1 | 296.6 | 255.5 | 348.5 | 1.364 | 2.2 | 1.1 |
| | 10 | 41.1 | 298.1 | 257.0 | 350.5 | 1.364 | 2.8 | 1.1 |
| | 20 | 41.1 | 308.6 | 267.5 | 351.8 | 1.315 | 7.0 | 4.6 |
| Antibiotic trans-BM123γ Sample #3 | 5 | 41.1 | 296.0 | 255.0 | 346.5 | 1.359 | 2.0 | 1.5 |
| | 10 | 41.1 | 302.1 | 261.1 | 352.7 | 1.351 | 4.4 | 2.0 |
| | 20 | 41.1 | 307.4 | 266.3 | 348.6 | 1.309 | 6.5 | 5.1 |

TABLE VII

Evaluation of the Efficacy of trans-BM123γ-hydrochloride as a Feed Additive for the Enhancement of the Growth Rate of Poultry and for Improving Feed Efficiency.

| Treatment | Drug Level in Feed (ppm) | Average weight per Chick in Gram Start | Average weight per Chick in Gram End | Average weight gain per Chick in Gram | Feed Consumed per Chick in Gram (Average) | Feed Gain Ratio | Percent Improvement in Gain | Percent Improvement in Feed/Gain Ratio |
|---|---|---|---|---|---|---|---|---|
| Control | 0 | 41.3 | 284.1 | 242.8 | 338.0 | 1.392 | | |
| | 10 | 41.3 | 292.0 | 250.7 | 343.7 | 1.371 | 3.3 | 1.5 |
| #1 | 20 | 41.3 | 296.2 | 254.9 | 340.8 | 1.337 | 5.0 | 3.9 |
| | 40 | 41.3 | 298.2 | 256.9 | 339.1 | 1.320 | 5.8 | 5.2 |
| | 5 | 41.3 | 285.0 | 243.7 | 332.7 | 1.365 | 317 | 1.9 |
| #2 | 10 | 41.3 | 295.1 | 253.8 | 344.4 | 1.357 | 5.0 | 2.5 |
| | 20 | 41.3 | 302.4 | 261.1 | 339.4 | 1.300 | 5.8 | 6.6 |
| | 5 | 41.3 | 291.7 | 250.4 | 344.3 | 1.375 | 3.1 | 1.2 |
| #3 | 10 | 41.3 | 295.6 | 254.3 | 343.3 | 1.350 | 4.7 | 3.0 |
| | 20 | 41.3 | 301.3 | 260.0 | 347.9 | 1.338 | 7.1 | 3.9 |
| #4 | 5 | 41.3 | | 248.8 | | 1.37 | 2.5 | 1.6 |
| | 10 | 41.3 | | 260.9 | | 1.33 | 7.5 | 4.5 |
| | 20 | 41.3 | | 255.6 | | 1.34 | 5.3 | 3.7 |
| | 40 | 41.3 | | 254.9 | | 1.35 | 5.0 | 2.9 |

EXAMPLE 8

Evaluation of the efficacy of trans-BM123β sodium lauryl sulfate complex in improving the growth rate and feed efficiency of weanling pigs.

Test Animals

Forty, five week old weanling pigs are allotted randomly into 4 groups of 10 pigs each. One group serves as unmedicated controls. The other groups receive the drug in their diet at the levels indicated in Table VIII below.

Procedure

Control animals are offered a modified pig starter ration (composition of same is appended hereto) and water ad libitum. The other groups receive the same diet except that it is medicated with the test drug at the levels indicated.

The weight of the pigs is determined at the start and two weeks later. Further, average daily weight gains, average overall weight gains, weight of feed consumed per pen, feed/gain ratios, and the percent improvements (over controls) of weight gains and feed/gain ratios are also determined. The thus obtained data are summarized in Table VIII below.

| Modified Pig Starter Ration | |
|---|---|
| Composition | lb/ton |
| Corn | 1250 |
| Farm Blend Protein Supplement* | 600 |
| Dried whey | 150 |
| | 2000 |

*Farm Blend Protein Supplement
Ingredients
Processed grain by-products, animal protein products, plant protein products, cane molasses, forage products, vitamin A supplement, D activated animal sterol, vitamin B12 supplement, vitamin E supplement, riboflavin supplement, methionine hydroxy analogue calcium, niacin, biotin, choline chloride, calcium pantothenate, defluorinated phosphate, calcium carbonate, iodized salt, sodium selenide, iron carbonate, iron sulfate, manganous oxide, copper sulfate, cobalt carbonate, zinc oxide.

| Analysis | |
|---|---|
| Crude protein not less than | 36.0% |
| Crude fat not less than | 0.5 |
| Crude fiber not more than | 7.0 |
| Calcium (Ca) not less than | 3.2 |
| Calcium (Ca) not more than | 4.2 |
| Phosphorus (P) not less than | 1.7 |
| Iodine not less than | 0.0003 |
| Salt (NaCl) not less than | 2.3 |
| Salt (NaCl) not more than | 3.3 |

TABLE VIII

Efficacy of trans-BM123γ-sodium lauryl sulfate complex in improving the growth rate and feed efficiency in weanling pigs. Two weeks feeding data, averaged.

| Group | Drug level in Diet (ppm) | Average Weight per pig in kg Start | Average Weight per pig in kg Finish | Average weight gain per pig in kg Two weeks | Average weight gain per pig in kg Daily | % Improvement over Control | Total Feed per pen in kg | Feed/Gain Ratio | % Improvement over Control |
|---|---|---|---|---|---|---|---|---|---|
| Control | 0 | 8.45 | 13.55 | 5.13 | 0.366 | | 95.2 | 1.855 | |
| 1 | 25 | 8.31 | 14.95 | 6.66 | 0.476 | 30 | 114.8 | 1.768 | 5 |
| 2 | 50 | 8.15 | 14.70 | 6.57 | 0.469 | 28 | 103.3 | 1.572 | 15 |
| 3 | 100 | 8.52 | 15.80 | 7.3 | 0.521 | 42 | 117.8 | 1.613 | 13 |

EXAMPLE 9

Preparation of Antibiotic trans-BM-123γ - Lauryl Sulfate Complex from Whole Harvest Mash A 28 liter portion of Nocardia s.p. NRRL 11,230 fermentation mash containing 571 mcg. of antibiotic trans-BM123 per ml. is adjusted to pH 2.0 with dilute sulfuric acid. A 218 g. portion of sodium lauryl sulfate is added and the pH is readjusted to 2.0 with dilute sulfuric acid. The mixture is stirred for 45 minutes, 60 g. of diatomaceous earth is added and the mixture is filtered. The solid complex is dried in vacuo at 40° C. for 67 hours giving 1.4 kg. of material containing the antibiotic trans-BM123γ complex.

Nocardia sp. NRRL 11,230 has cultural, physiological, and morphological characteristics essentially the same as those of NRRL 5646 and NRRL 8050.

EXAMPLE 10

Preparation of Antibiotic trans-BM123γ - Lauryl Sulfate Complex from Harvest Mash Filtrate To 6 liters of Nocardia sp. NRRL 11,230 fermentation mash filtrate containing 447 mcg. of antibiotic trans-BM123γ per ml. there is added with stirring 90.0 g. of diatomaceous earth followed by 420 ml. of 10% w/v aqueous sodium lauryl sulfate. The pH of the suspension is adjusted to 2.5 with 50% w/w sulfuric acid, stirred or 15 minutes and then filtered. The filter cake is rinsed with a small amount of water and then dried for three days in vacuo with heat, giving 223.4 g of product assaying 4.9 mcg./mg.

EXAMPLE 11

Preparation of Antibiotic trans-BM123γ - Dioctyl Sodium Sulfosuccinate Complex from Harvest Mash Filtrate To a liter portion of Nocardia sp. NRRL 11,230 fermentation mash filtrate containing 533 mcg. of antibiotic trans-BM123γ per ml., is added 800 g. of sodium chloride. The filtrate is adjusted to pH 4 with hydrochloric acid. A 600 g. portion of diatomaceous earth is added followed by one liter of an aqueous alcoholic solution of dioctyl sodium sulfosuccinate. The pH is readjusted to 4.0 with hydrochloric acid, 600 g. of diatomaceous earth is added and the mixture is stirred for 15 minutes. The mixture is allowed to settle for one hour and the supernatant is symphoned off. The pH of the settled material is adjusted to 5 with sodium hydroxide. The mixture is then freeze dried giving 3.02 kg. of material containing antibiotic trans-BM123γ - dioctyl sodium sulfosuccinate complex.

EXAMPLE 12

Preparation of Antibiotic trans-BM123γ - Dioctyl Sodium Sulfosuccinate Complex from Harvest Mash Filtrate To a 100 ml. portion of Nocardia sp. NRRL 11,230 mash filtrate, assaying 582 mcg./ml. of antibiotic trans-BM123γ, is added with stirring 1.0 ml. of a 70% ethanolic solution of dioctyl sodium sulfosuccinate. The pH of the mixture is adjusted to 4.75 with 6N hydrochloric acid and the mixture is centrifuged. The supernatant is decanted and the precipitate is dried in vacuo for 4 days without heat to give 1.5 g. of product.

EXAMPLE 13

Preparation of Antibiotic trans-BM123γ - Syntan Complex from Whole Harvest Mash

Thirty liters of Nocardia sp. NRRL 11,230 fermentation mash containing 347 mcg. of trans-BM123γ - antibiotic per ml. is used at harvest pH 5.7. A 750 ml. portion of Trutan RT New [a synthetic tanning agent (A. J. and J. O. Pilar, Inc.)] is added slowly to the mash with stirring. The mixture is stirred for one hour, 600 g. of diatomaceous earth is added and the mixture is filtered. The filter cake is dried in vacuo at 40° C. for 48 hours, giving 1.5 kg. of dried material containing the antibiotic trans-BM123γ complex.

EXAMPLE 14

Preparation of Antibiotic trans-BM123γ - Syntan Complex from Harvest Mash Filtrate To 3 liters of stirred Nocardia sp. NRRL 11,230 fermentation mash filtrate, assaying 475 mcg. of antibiotic trans-BM123γ per ml. is added 52.5 ml. of Trutan RT New. The pH of the resultant slurry is adjusted to 4.75 with 6N hydrochloric acid, stirred for 5 minutes and allowed to settle for 45 minutes. The solids are recovered by filtration, washed with a small amount of water and dried in vacuo, without heat, giving 35.8 g. of product.

EXAMPLE 15

Evaluation of certain trans-BM123γ-alkyl derivatives as feed additives for the enhancement of the growth rate of poultry

Test Drugs

1. Antibiotic trans-BM123γ-HCl (60%).
2. Antibiotic trans-BM123γ-HCl, spray dried filtrate (0.933%).
3. Antibiotic trans-BM123γ-sodium lauryl sulfate (0.447%).
4. Isopropyl-trans-BM123γ.
5. 1-Methylnonyl-trans-BM123γ.
6. 1,3-Dimethylbutyl-trans-BM123γ.
7. 1,1,3-Trimethylbutyl-trans-BM123γ.
8. 1-Ethyl-3-chloropropyl-trans-BM123γ.
9. 1,2-Dimethylpentyl-trans-BM123γ.
10. 1-Methyl-2-hydroxypropyl-trans-BM123γ.

Test Animals

One day old Hubbard X Hubbard crossbred chicks, randomly allotted to pens of ten chicks (5 males and 5 females) each.

Procedure

The procedure of Example 3 is used. The duration of each experiment is 14 days.

The data obtained are averaged and summarized in Table IX below.

TABLE IX

Evaluation of the Efficacy of Certain BM123γ-alkyl derivatives for the Enhancement of the Growth Rate of Poultry and for Improving Feed Efficiency.

| Treatment | Drug Level in Feed (ppm) | Average weight per Chick in Gram | | Average weight gain per Chick in Gram | Feed Consumed per Chick in Gram (Average) | Feed/Gain Ratio | Percent Improvement in | |
|---|---|---|---|---|---|---|---|---|
| | | Start | End | | | | Gain | Feed/Gain Ratio |
| Control | 0 | 37.3 | 272.5 | 235.2 | 329.5 | 1.401 | | |
| | 5 | 37.3 | 276.7 | 239.4 | 333.9 | 1.395 | 1.78 | 0.43 |
| #1 | 10 | 37.3 | 280.6 | 243.3 | 328.7 | 1.351 | 3.74 | 3.57 |

TABLE IX-continued
Evaluation of the Efficacy of Certain BM123γ-alkyl derivatives for the Enhancement of the Growth Rate of Poultry and for Improving Feed Efficiency.

| Treatment | Drug Level in Feed (ppm) | Average weight per Chick in Gram Start | Average weight per Chick in Gram End | Average weight gain per Chick in Gram | Feed Consumed per Chick in Gram (Average) | Feed/Gain Ratio | Percent Improvement in Gain | Percent Improvement in Feed/Gain Ratio |
|---|---|---|---|---|---|---|---|---|
|  | 20 | 37.3 | 291.4 | 254.1 | 346.2 | 1.363 | 8.04 | 2.71 |
|  | 5 | 37.3 | 285.4 | 248.1 | 334.9 | 1.350 | 5.48 | 3.64 |
| #2 | 10 | 37.3 | 284.3 | 247.0 | 332.6 | 1.347 | 5.02 | 3.85 |
|  | 20 | 37.3 | 292.1 | 254.8 | 340.0 | 1.334 | 8.33 | 4.78 |
| #3 | 10 | 37.3 | 288.2 | 250.9 | 328.6 | 1.310 | 6.68 | 6.50 |
|  | 5 | 37.3 | 281.8 | 244.5 | 331.4 | 1.355 | 3.95 | 3.28 |
| #4 | 10 | 37.3 | 283.1 | 245.8 | 328.2 | 1.335 | 4.51 | 4.71 |
| #5 | 10 | 37.3 | 282.6 | 245.3 | 334.0 | 1.362 | 4.29 | 2.78 |
| #6 | 10 | 37.3 | 283.8 | 246.5 | 334.1 | 1.358 | 4.80 | 3.07 |
| #7 | 10 | 37.3 | 282.2 | 244.9 | 333.4 | 1.361 | 4.12 | 2.86 |
| #8 | 5 | 37.3 | 276.6 | 239.3 | 328.9 | 1.375 | 1.74 | 1.86 |
| #9 | 10 | 37.3 | 279.8 | 242.5 | 334.7 | 1.380 | 3.10 | 1.50 |
| #10 | 10 | 37.3 | 280.4 | 243.1 | 331.5 | 1.364 | 3.76 | 2.64 |

The pamoate complex useful in the invention is described in application Ser. No. 70,460 of Tobkes and Dann et al filed concurrently herewith. In the following description of the pamoate complex, BM123-gamma refers to a mixture in any proportions of BM123-gamma, and BM123-gamma₂, as well as the individual components. The pamoate complex is prepared by precipitation of the antibiotic either from the whole harvest mash, the filtered fermentation broth or solutions of partially purified recovered antibiotic by the addition of ammonium pamoate, an alkaline earth metal pamoate such as disodium pamoate which is commercially available and whose structure is given below.

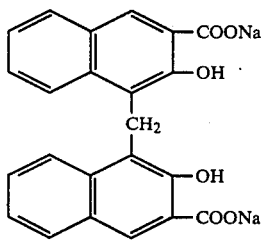

The process of manufacturing the pamoate provides almost complete removal of the antibiotic activity from the fermentation mash or broth. Furthermore, the antibiotic-pamoate complex so obtained can be used, without separation of the constituents, in animal feed supplement compositions, which is an important economic advantage.

The product of the antibiotic and the alkali metal pamoate is a reversible complex. Its exact chemical nature has not been determined. While it is not intended to limit the present invention to theories of chemical constitution, it seems probable that the complex of the present invention is sufficiently reversible so that under conditions of use in animal feed supplement compositions the antibiotic is set free upon ingestion.

As starting material for the manufacturing process of the pamoate complex there may be employed the whole harvest mash obtained after completion of a fermentation producing antibiotic BM123-gamma as described in U.S. Pat. No. 4,007,167. Preferably there is employed the fermentation liquor or broth which has been clarified by removing the mycelia and other insolubles by filtration. Diatomaceous earth or any other conventional filtration aid may be used to assist in the filtration.

In general, the procedure comprises the addition of a pamoate salt solution to stirred whole harvest mash or filtered broth at ambient temperature while maintaining the pH at between 4.0 and 8.0 by addition of dilute aqueous acid or base. Suitable acids for this purpose may be, for example, dilute hydrochloric acid, dilute sulfuric acid, dilute trifluoroacetic acid, etc., although even glacial acetic acid may be used. Suitable bases include ammonium hydroxide and the alkali and alkaline earth hydroxides, carbonates and bicarbonates. The precipitated pamoate complex, or in the case of the whole mash the precipitated pamoate complex together with the fermentation mash solids, is recovered by filtration or centrifugation and dried. The products so obtained may be washed by slurrying the wet solids in polar, water miscible liquids such as acetone (which do not act as solvents for the complex) followed by filtration, rinsing and air-drying or by reslurrying the wet solids in water and freeze-drying, spray-drying or oven drying.

When the products are thus carefully dried under temperature conditions which do not degrade antibiotic BM123γ, they are usually gray to tan to brown solids in the case of the pamoate complex.

It is an advantage that the amount of pamoate added to precipitate the complex with the antibiotic is not critical and no exact stoichiometric relations need be followed. In general, the amount of pamoate used will be in excess of the minimum required to form the complex with the antibiotic in order to ensure complete precipitation. The specific bioactivity of the precipitated complex varies and it is, in fact, likely that the complex has varying relative amounts of antibiotic to pamoate.

The minimum amount of pamoate required to form the complex with the antibiotic in any particular fermentation batch may be readily determined as follows. A sample (conveniently 50-100 ml.) of the fermentation whole harvest mash is taken and clarified by removing the mycelia and other insolubles by filtration, preferably with a filter aid. The filtrate is then adjusted to a pH of 4.0 to 8.0 with dilute aqueous mineral acid or base, and then titrated with the particular aqueous solution of pamoate which is to be used, until no further precipitate or turbidity forms. The amount of pamoate solution for the fermentation batch is then calculated from the titer of the sample taken, providing also for a slight excess.

The feed supplement compositions are administered in an amount sufficient to furnish approximately the following dosage levels in mg./head/day:
Large ruminants—350
Small ruminants—200
Non-ruminants—100
Poultry—2

The milligrams per pound of antibiotic BM123γ present in any particular supplement composition may be readily determined by bioassay as set forth in U.S. Pat. No. 4,007,167. The preferred method is an adaptation of the *Staphylococcus aureus* turbidimetric assay for tetracycline that is described in the manual "Assay Methods of Antibiotics, A Laboratory Manual" by D. C. Grove and W.A. Randall, Medical Encyclopedia Inc. (1955), pages 48–52, substituting *Klebsiella pneumoniae* as the test organism. From the potency data thus obtained, the pounds of food supplement composition to be used per ton of feed may be readily calculated.

A wide variety of carriers may be used in the preparation of the feed supplement compositions containing the dried antibiotic BM123γ pamoate complex or the dried harvest mash solids containing the complex. Carriers suitable for use to make up the feed supplement compositions include the following: soybean meal, alfalfa meal, cotton seed oil meal, linseed oil meal, cornmeal, cane molasses, urea, bone meal, corncob meal, and the like. The carrier promotes a uniform distribution of the complex in the finished feed into which the supplement is blended. It thus performs an important function by ensuring proper distribution of the complex throughout the feed.

Specific examples of the pamoate complexes are set forth below. These examples are merely illustrative and are not to be construed as limiting the scope and underlying principles of the invention in any way.

EXAMPLE 16

Preparation of Antibiotic BM123γ Pamoate Complex From Harvest Mash Filtrate

To a 320 liter portion of fermentation mash containing BM123γ at pH 5.2, is added 640 g. (0.2%) of sodium fluoride. The pH is adjusted to 6.0–6.25 with sodium hydroxide and the mixture is stirred for one hour. A 16 kg. portion of filter aid (Hyflo-Supercel) is added and the mixture is filtered. The filtrate is adjusted to pH 4.7–4.8 with hydrochloric acid and 6400 ml. of Amberlite IRC-72 ($Na^+$) resin (Rohm & Haas, Inc.) is gradually added. The pH is adjusted to 4.7–4.9 with hydrochloric acid, the mixture is stirred for 2 hours and allowed to stand overnight. The supernatant is syphoned off and discarded. The resin is transferred to a 10.16 cm.×121.92 cm. glass column having a bed volume of about 4.8 liters. The bed is washed with two bed volumes of pH 4.5 sodium acetate-acetic acid buffer solution (8 g. of sodium acetate per liter of water adjusted to pH 4.5 with glacial acetic acid). Then the resin is washed with two additional bed volumes of the same buffer and this wash is collected separately, adjusted to pH 4.0 with glacial acetic acid and put through the resin bed again. The resin is then washed with 20 liters of water. The antibiotic activity is eluted from the column with 0.02–0.025 N hydrochloric acid, collecting one liter fractions and monitoring the fractions by ultraviolet absorption at 286 nm for antibiotic activity. A total of 97 liters of active eluate are pooled. Thirty-two liters of this eluate are adjusted from pH 2.1 to pH 4.7–4.8 with sodium hydroxide and 480 g. of perlite filter aid are added. A solution of 50 g. of pamoic acid disodium salt in 625 ml. of water is prepared and a total of 555 ml. is added in approximately 50 ml. increments, adjusting the pH to 4.7–4.8 with 10 N sulfuric acid after each addition. A 480 g. portion of perlite is added and the mixture is filtered on a filter press. The damp cake is dried in a vacuum oven at 38°–40° C. and then ground in a comminuting machine giving 997 g. of product which bioassayed 3.5% as BM123γ in an auto turbidimetric method against *Klebsiella pneumoniae*.

EXAMPLE 17

Preparation of Antibiotic BM123γ Pamoate Complex From Harvest Mash Filtrate

To a 3000 liter portion of fermentation mash containing BM123γ is added 6 kg. of sodium fluoride. The mixture, at pH 5.5–506, is stirred for about ½ hour and 150 kg. of filter aid (Hyflo-Supercel) is added. The mixture is filtered through a plate-frame filter press. The first 700 liters of clarified filtrate are collected and adjusted to pH 4.5–4.8 with hydrochloric acid. The antibiotic activity is absorbed batchwise with Amberlite IRC-72 ($Na^+$) (Rohm & Haas, Inc.) resin used at a rate of 30 ml. of resin/liter of filtrate. The resin is added gradually to the filtrate with constant stirring and the pH of the mixture is maintained at 4.5–4.8 with hydrochloric acid. After addition is complete, the mixture is stirred for about 3 hours and the resin is allowed to settle overnight. The supernatant is syphoned off and the 17.9 liters of resin are transferred to a 15.24 cm.×152.4 cm. glass column. The resin is washed with two bed volumes of sodium acetate-acetic acid buffer (8 g. of sodium acetate per liter of water, adjusted to ph 4.0 with glacial acetic acid). This wash is repeated with a fresh two bed volume of the buffer. This second wash is collected, adjusted to pH 4.0 with glacial acetic acid, and again passed through the resin. The resin is washed with four bed volumes of water and then eluted with 0.03–0.05 N hydrochloric acid monitoring for activity by ultraviolet absorption at 286 nm. The active fractions are pooled, adjusted to pH 5.0–5.3 by addition of Amberlite IRA-45 resin (Rohm & Haas, Inc.). After standing, the supernatant is syphoned off and concentrated at reduced pressure to a volume of 12 liters. A 2 liter portion of this concentrate is adjusted to pH 4.7–4.8 with 10 N sulfuric acid. To this is added, in increments, a solution of 125 g. of pamoic acid disodium salt in 1562.5 ml. of water, with constant stirring, maintaining the pH at 4.7–4.8 with 10 N sulfuric acid. The precipitate is collected by centrifugation, suspended in water and freeze-dried, giving 215.5 g. of dried product which bioassays 27% as BM123γ in an auto turbidimetric method against *Klebsiella pneumoniae*.

EXAMPLE 18

Preparation of Antibiotic BM123γ Sodium Pamoate Complex

A 7.00 g. portion of antibiotic BM123γ is dissolved in 200 ml. of water. A total of 70 ml. of 7.5% w/v sodium pamoate solution at pH 10.2 is added, the pH is adjusted to 4.75 with 10 N sulfuric acid and the mixture is centrifuged. The precipitate is dried in vacuo at room temperature and assayed turbidimetrically at 512 mcg./mg. antibiotic BM123γ.

EXAMPLE 19

Precipitation of Antibiotic BM123γ Pamoate From Whole Harvest Mash

To 100 ml. of stirred fermentation mash containing BM123γ there is added 15 ml. of a 10% w/v solution of sodium pamoate while maintaining the pH at 4.7 by the simultaneous addition of 50% sulfuric acid. After stirring 5 minutes, the suspension is centrifuged and after removing the supernatant the residue is dried in vacuo at 40° C. to give 5.59 g. of a solid which bioassays 3.21 mcg./mg. as BM123γ in an auto turbidimetric method against *Klebsiella pneumoniae*.

EXAMPLE 20

Precipitation of Antibiotic BM123γ Pamoate From Harvest Mash Filtrate

To 600 ml. of stirred fermentation mash containing BM123γ there is added diatomaceous earth and the mixture is filtered. To 100 ml. of this filtrate there is added, with stirring, 15 ml. of a 10% w/v solution of sodium pamoate while simultaneously maintaining the pH of the mixture at 4.7 by the addition of 50% sulfuric acid. The resultant precipitate is centrifuged off and dried in vacuo at 40° C. to give 4.72 g of product which bioassays 3.07 mcg./mg. as BM123γ in an auto turbidimetric method against *Klebsiella pneumoniae*.

EXAMPLE 21

Growth Promoting Effect of Antibiotic BM123γ Pamoate Complex on Poultry

One day old Hubbard X Ross crossbred chicks are used. These chicks are randomly allotted to pens of ten chicks (5 male and 5 female) each. In each experiment three pens of chicks are used for unmedicated controls and for each level of drug. The duration of each experiment is 14 days.

The controls are offered an unmedicated diet of broiler ration (composition follows) and water ad libitum. The medicated chicks are offered the same diet containing antibiotic BM123γ pamoate complex at a level of 20 parts per million and water ad libitum. The weight of the chicks is determined at the beginning and on completion of the experiments. Weight gain and the amount of feed consumed are also determined. The data are averaged and summarized in Table I below, together with the percent improvement in weight gains and feed/gain ratios.

| Broiler Ration Formula: | |
|---|---|
| Component | Percent by Weight |
| Ground yellow corn | 53.45 |
| Soybean oil meal (49%) | 28.00 |
| Menhaden fish meal (60%) | 5.00 |
| Corn gluten meal (60%) | 5.00 |
| Dehydrated alfalfa meal (17%) | 2.00 |
| Stabilized fat | 4.00 |
| Dicalcium phosphate | 1.20 |
| Ground limestone | 0.50 |
| Sodium chloride | 0.30 |
| Trace minerals mixture* | 0.05 |
| Vitamin premix** | 0.50 |

*Trace Mineral Mixture

| Component | | One lb./ton Furnishes |
|---|---|---|
| Manganese | 12.50% | 62.5 ppm. |
| Iron | 6.00% | 30.0 ppm. |
| Lime | 5.00% | 25.0 ppm. |
| Copper | 0.65% | 3.25 ppm. |
| Iodine | 0.35% | 1.75 ppm. |
| Cobalt | 0.25% | 1.25 ppm. |
| Calcium (min. 15.30%, max. 18.35%) | | |

**Vitamin Premix for One Ton

| Component | Weight In gm. |
|---|---|
| DL methionine | 453.6 |
| Butylated hydroxy toluene | 113.6 |
| Vitamin A (30,000 mcg./g.) | 100.0 |
| Vitamin $D_3$ (200,000 mcg./g.) | 5.0 |
| Vitamin E (20,000 mcg./lb.) | 45.4 |
| Riboflavin | 4.0 |
| Niacinamide | 25.0 |
| Calcium pantothenate | 8.0 |
| Vitamin K (menadione) | 1.0 |
| Folic acid (10%) | 13.0 |
| Choline chloride (50%) | 908.0 |
| Vitamin $B_{12}$ (20 mg./lb.) | 227.0 |
| Corn oil | 50.0 |
| Fine ground corn | 2582.4 |

TABLE X

| Treatment | Drug Level in Feed ppm. | Average Weight Per Chick in Grams | | Average Weight Gain Per Chick in Grams | Feed Consumed Per Chick in Grams (Average) | Feed/Gain Ratio | % Improvement Over Control in | |
|---|---|---|---|---|---|---|---|---|
| | | Start | End | | | | Weight Gain | Feed/Gain Ratio |
| Control | 0 | 36.3 | 238.7 | 202.5 | 321.2 | 1.586 | — | — |
| Antibiotic BM123γ pamoate complex | 20 | 36.2 | 260.6 | 224.4 | 340.0 | 1.533 | 10.8 | 3.3 |
| Antibiotic BM123γ pamoate complex | 20 | 36.2 | 257.7 | 221.5 | 338.0 | 1.526 | 9.4 | 3.8 |
| Control | 0 | 39.7 | 249.7 | 210.0 | 338.1 | 1.610 | — | — |
| Antibiotic BM123γ pamoate complex | 20 | 39.7 | 267.7 | 228.0 | 352.9 | 1.548 | 8.6 | 3.9 |
| Antibiotic BM123γ pamoate complex | 20 | 36.3 | 251.9 | 215.5 | 331.7 | 1.539 | 6.4 | 3.0 |

EXAMPLE 22

A BM123γ pamoate complex, isolated by a procedure similar to that described in Example 19, is "stress-tested" by heating for 8 hours at 70° C. Bioassays show that 70% of the active material remains after stressing. In contrast, when BM123γ is isolated by the addition of sodium lauryl sulfate solution and the resulting BM123γ lauryl sulfate complex "stress-tested" in exactly the same manner, only 18% of the active material can be found by bioassay.

EXAMPLE 23

A filtrate containing BM123γ, isolated as described in Example 20, is treated as follows: One portion is spray-dried. A second portion is treated with sodium pamoate solution and the precipitate is isolated by filtration and dried. A third portion is treated with sodium lauryl sulfate solution and the precipitate is filtered and dried. Each of these three products is mixed with animal feed and the mixtures are formed into pellets. The stability of these pellets is summarized below, with the recovery of active BM123γ being expressed as percent recovery of the amount of active ingredient added to the animal feed product.

| Treatment | % Recovery at 37° C. | |
|---|---|---|
| | Two Weeks | Four Weeks |
| Spray-dried | 31 | 17 |
| Sodium lauryl sulfate | 52 | 40 |
| Sodium pamoate | 78 | 51 |

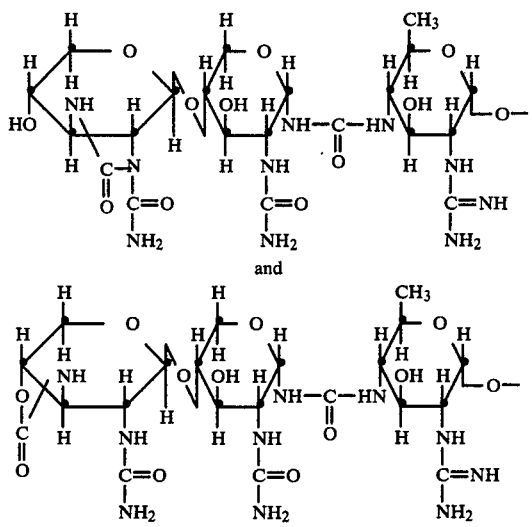

We claim:

1. A method for improving feed efficiency and enhancing the growth rate of meat animals comprising administering orally to the animals an effective amount of an antibacterial ingredient of antibiotic trans-BM123γ, an antibiotic trans-BM123γ salt, an antibiotic trans-BM123γ alkyl sulfate complex, an antibiotic trans-BM123γ dioctyl sulfosuccinate complex, an antibiotic trans-BM123γ syntan complex, an antibiotic trans-BM123γ pamoate complex, an antibiotic trans-BM123γ alkylated derivative, and mixtures thereof in any proportion.

2. A method according to claim 1 wherein the antibacterial ingredient is administered in amount from about 0.1 mg./kg. to about 25 mg/kg of body weight per day.

3. A method according to claim 1 wherein the meat animals are chickens, turkeys, cattle, sheep, goats and swine.

4. A method according to claim 1 wherein the antibiotic trans-BM123γ salt is hydrochloride, sulfate, phosphate, citrate and tartrate.

5. A method according to claim 1 wherein the antibiotic trans-BM123γ alkyl sulfate complex is the sodium lauryl sulfate complex.

6. A method according to claim 1 wherein the antibacterial ingredient is the antibiotic trans-BM123γ pamoate complex.

7. A method according to claim 1 wherein the alkylated derivatives of antibiotic trans-BM123γ may be represented by the following structural formula:

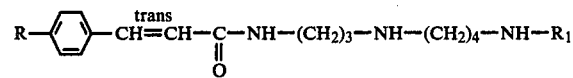

wherein $R_1$ is alkyl $C_1-C_{10}$, halo substituted alkyl $C_2-C_6$ or hydroxy substituted alkyl $C_2-C_6$ and wherein R is a moiety of the formula:

8. A method according to claim 7 wherein $R_1$ is isopropyl, 1,3-dimethylbutyl, 1,1,3-trimethylbutyl, 1,2-dimethylpentyl, 1-methylnonyl, 1-ethyl-3-chloropropyl and 1-methyl-2-hydroxypropyl.

9. A method according to claim 1 wherein the animals are chickens, cattle or sheep and the antibacterial ingredient is administered in amounts from about 0.1 mg/kg to about 20 mg/kg of body weight daily.

10. A method according to claim 1 wherein the animals are swine and the antibacterial ingredient is administered in amounts from about 0.2 mg/kg to about 15 mg/kg of body weight daily.

11. A method for improving feed efficiency and enhancing the growth rate of meat animals comprising administering orally to the animals an effective amount of an antibactrial ingredient of antibiotic cis-BM123γ, an antibiotic cis-BM123γ salt, an antibiotic cis-BM123γ alkyl sulfate complex, an antibiotic cis-BM123γ dioctyl sulfosuccinate complex, an antibiotic cis-BM123γ complex, an antibiotic cis-BM123γ pamoate complex, an antibiotic cis-BM123γ alkylated derivative, and mixtures thereof in any proportion.

12. A method according to claim 11 wherein the antibacterial ingredient is administered in amount from about 0.1 mg./kg. to about 25 mg/kg of body weight per day.

13. A method according to claim 11 wherein the meat animals are chickens, turkeys, cattle, sheep, goats and swine.

14. A method according to claim 11 wherein the antibiotic cis-BM123γ salt is the hydrochloride, sulfate, phosphate, citrate and tartrate.

15. A method according to claim 11 wherein the antibiotic cis-BM123γ alkyl sulfate complex is the sodium lauryl sulfate complex.

16. A method according to claim 11 wherein the antibacterial ingredient is the antibiotic cis-BM123γ pamoate complex.

17. A method according to claim 11 wherein the alkylated derivatives of antibiotic cis-BM123γ may be represented by the following structural formula:

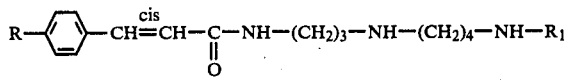

wherein $R_1$ is alkyl $C_1$-$C_{10}$, halo substituted alkyl $C_2$-$C_6$ or hydroxy substituted alkyl $C_2$-$C_6$ and wherein R is a moiety selected from the group consisting those of the formula:

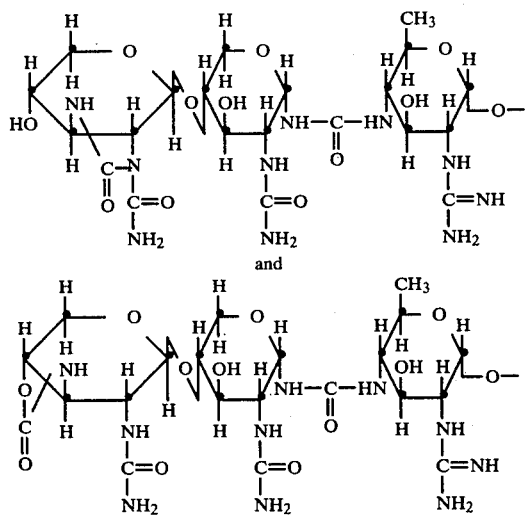

18. A method according to claim 17 wherein $R_1$ is isopropyl, 1,3-dimetylbutyl, 1,1,3-trimethylbutyl, 1,2-dimethylpentyl, 1-methylnonyl, 1-ethyl-3-chloropropyl and 1-methyl-2-hydroxypropyl.

19. A method according to claim 11 wherein the animals are chickens, cattle or sheep and the antibacterial ingredient is administered in amounts from about 0.1 mg/kg to about 20 mg/kg of body weight daily.

20. A method according to claim 11 wherein the animals are swine and the antibacterial ingredient is administered in amounts from about 0.2 mg/kg to about 15 mg/kg of body weight daily.

21. A method for improving feed efficiency and enhancing the growth rate of meat animals comprising administering orally to the animals an effective amount of an antibacterial ingredient of antibiotic cis-BM123γ and antibiotic trans-BM123γ, a mixture of salts of the antibiotics, a mixture of alkyl sulfate complexes of the antibiotics, a mixture of dioctyl sulfosuccinate complexes of the antibiotics, a mixture of syntan complexes of the antibiotics, a mixture of pamoate complexes of the antibiotics, a mixture of alkylated derivatives of the antibiotics, and mixtures thereof in any proportion.

22. A method according to claim 21 wherein the antibacterial ingredient is administered in amount from about 0.1 mg/kg to about 25 mg/kg of body weight per day.

23. A method according to claim 21 wherein the meat animals are chickens, turkeys, cattle, sheep, goats and swine.

24. A method according to claim 21 wherein the salts are the hydrochloride, sulfate, phosphate, citrate and tartrate.

25. A method according to claim 21 wherein the alkyl sulfate complexes are the sodium lauryl sulfate complexes.

26. A method according to claim 21 wherein the alkylated derivatives may be represented by the following structural formula:

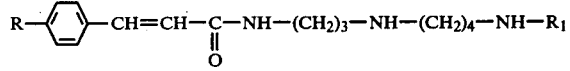

wherein $R_1$ is alkyl $C_1$-$C_{10}$, halo substituted alkyl $C_2$-$C_6$ or hydroxy substituted alkyl $C_2$-$C_6$ and wherein R is a moiety of the formula:

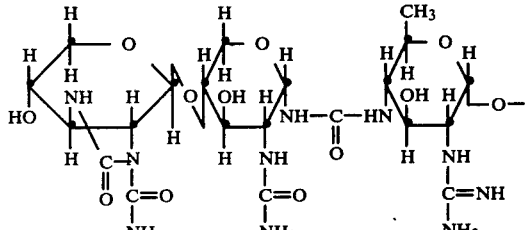
and
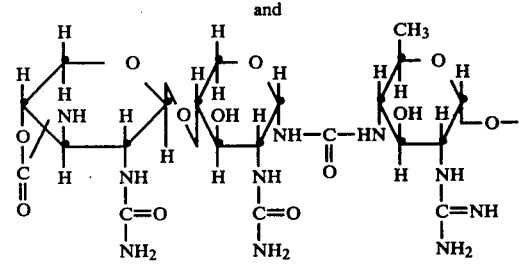

27. A method according to claim 26 wherein $R_1$ is isopropyl, 1,3-dimethylbutyl, 1,1,3-trimethylbutyl, 1,2-dimethylpentyl, 1-methylnonyl, 1-ethyl-3-chloropropyl and 1-methyl-2-hydroxypropyl.

28. A method according to claim 19 wherein the animals are chickens, cattle or sheep and the antibacterial ingredient is adminisered in amounts from about 0.1 mg/kg to about 20 mg/kg of body weight daily.

29. A method according to claim 21 wherein the animals are swine and the antibacterial ingredient is administered in amounts from about 0.2 mg/kg to about 15 mg/kg of body weight daily.

* * * * *